(12) United States Patent
Hickey

(10) Patent No.: US 8,535,919 B2
(45) Date of Patent: Sep. 17, 2013

(54) PROCESS FOR CONVERTING GAS STREAM COMPRISING CO, $CO_2$ AND $H_2$ TO LIQUID PRODUCTS BY FERMENTATION

(75) Inventor: Robert Hickey, Okemos, MI (US)

(73) Assignee: Coskata, Inc., Warrenville, IL (US)

( * ) Notice: Subject to any disclaimer, the term of this patent is extended or adjusted under 35 U.S.C. 154(b) by 453 days.

(21) Appl. No.: 12/826,968

(22) Filed: Jun. 30, 2010

(65) Prior Publication Data

US 2012/0003706 A1 Jan. 5, 2012

(51) Int. Cl.
*C12P 7/54* (2006.01)
*C12P 7/52* (2006.01)
*C12P 7/02* (2006.01)
*C12P 7/16* (2006.01)
*C12P 7/06* (2006.01)
*C12M 1/00* (2006.01)

(52) U.S. Cl.
USPC ........... 435/140; 435/141; 435/155; 435/160; 435/161; 435/289.1

(58) Field of Classification Search
None
See application file for complete search history.

(56) References Cited

U.S. PATENT DOCUMENTS

| | | |
|---|---|---|
| 4,162,970 A | 7/1979 | Zlokarnik |
| 4,426,450 A | 1/1984 | Donofrio |
| 4,683,122 A | 7/1987 | Concordia et al. |
| 5,173,429 A | 12/1992 | Gaddy et al. |
| 5,254,253 A | 10/1993 | Behmann |
| 6,136,577 A | 10/2000 | Gaddy |
| 6,551,805 B2 | 4/2003 | Ho et al. |
| 6,872,867 B1 | 3/2005 | Senetar |
| 7,285,402 B2 | 10/2007 | Gaddy |
| 2008/0176301 A1 | 7/2008 | Granda et al. |
| 2008/0299650 A1 | 12/2008 | Krieg |
| 2009/0035848 A1 | 2/2009 | Hickey |

FOREIGN PATENT DOCUMENTS

WO WO0208438 A2 1/2002

OTHER PUBLICATIONS

Worden et al., Mass-Transfer Properties of Microbubbles. 2. Analysis Using a Dynamic Model, 1998 American Chemical Society and American Institute of Chemical Engineers, Published on Web Jan. 14, 1998, Biotechnol. Prog. 1998. 74. 39-46.
Bloor et al., High Rate Aerobic Treatment of Brewery Wastewater Using the Jet Loop Reactor, Wat. Res. vol. 29, No. 5, pp. 1217-1223. 1995.
Bredwell et al., Mass-Transfer Properties of Microbubbles. 1. Experimental Studies, 1998 American Chemical Society and American Institute of Chemical Engineers, Published on Web Jan. 14, 1998, Biotechnol. Prog. 1998. 14. 31-38.
Bredwell et al., Reactor Design Issues for Synthesis-Gas Fermentations, 1999 American Chemical Society and American Institute of Chemical Engineers, Published on Web Oct. 1, 1999; Biotechnol. Prog. 1999, 15, 934-844.
Dursun et al., Mass transfer and hydrodynamic characteristics in a co-current downflow contacting column, 2003 Society of Chemical Industry; J Chem Technol Biotechnol 78:446-451 (online; 2003).
Engin et al., Modeling and Parameter Identification of a Jet-loop Bioreactor, Proceedings of the 2007 American Control Conference, Marriott Marquis Hotel at Times Square, New York City, USA, Jul. 11-13, 2007, FrC19.4, 6122-6127.
Fadavi et al., Gas-liquid mass transfer in a novel forced circulation loop reactor, Chemical Engineering Journal 112 (2005) 73-80.
Jamshidi et al., Studies on the hydrodynamic behavior and mass transfer in a down-flow jet loop reactor with a coaxial draft tube, 2001 Society of Chemical Industry; J Chem Technol Biotechnol 76: 39-46 (2001).
Krishna et al., Influence of Alcohol Addition on Gas Hold-Up in Bubble Columns: Development of a Scale Up Model, Int. Comm. Heat Mass Transfer, vol. 27, No. 4, pp. 465-472, 2000.
Kundu, et al., Experimental Studies on a Co-Current Gas-Liquid Downflow Bubble Column, Int. J. Multiphase Flaw, vol. 21, No. 5, pp. 893-906, 1995.
Mandal, et al., Gas-holdup distribution and energy dissipation in an ejector-induced downflow bubble column: the case of non-Newtonian liquid, Chemical Engineering Science 59 (2004) 2705-2713.
van Dierendonck, et al., Loop Venturi Reactor—A Feasible Alternative to Stirred Tank Reactors?, Ind. Eng. Chem. Res., vol. 3T No. 3. 1998, 734-738.
Rusten, B. et al., Design and Operations of the Kaldnes moving bed biofilm reactors, vol. 34, Issue 3, May 2006, pp. 322-331.

*Primary Examiner* — David M Naff

(57) ABSTRACT

A process converts a gas input stream comprising CO, $CO_2$, and $H_2$ by contact with fermentation liquid into a liquid product that controls the concentration of CO and $CO_2$ in the fermentation vessel. The process charges the feed gas stream and a recycle gas stream to the fermentation vessel and an off-gas stream collects above the fermentation liquid. The off-gas stream flows to a gas injector that uses a recycle liquid as the motive fluid to mix the off-gas with the recycle liquid into a gas-liquid dispersion. Contact of the recycle liquid with the off-gas absorbs $CO_2$ to provide the recycle stream. A gas separation vessel separates the remainder of the off-gas into the recycle gas. Mixing the recycle gas with the gas input stream dilutes the concentration of CO to lower the CO concentration in the fermentation vessel. Separated recycle liquid flows to a $CO_2$ stripper for removal of $CO_2$.

10 Claims, 3 Drawing Sheets

PROCESS FOR CONVERTING GAS STREAM COMPRISING CO, CO₂ AND H₂ TO LIQUID PRODUCTS BY FERMENTATION

FIELD OF THE INVENTION

This invention relates to the control of CO and $CO_2$ in the bioconversion of a CO, $CO_2$ and $H_2$ feed gas stream to liquid products such as bioethanol by contact with microorganisms in a deep fermentation vessel.

DETAILED DESCRIPTION

Background

Dispersing gas into liquid media is of particular interest in the field of fermentation due to the increased emphasis on the conversion of renewable energy sources into liquid products. For example conversion of biomass for biofuel production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology.

One technology path for the production of such biofuels is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be very efficient since the gasification step can convert all of the components to syngas with good efficiency (e.g., more than 75% of the energy can be available as fermentable compounds), and some strains of anaerobic microorganisms can convert syngas to ethanol, n-butanol or other chemicals with high (e.g., greater than 90% of theoretical) efficiency.

However, this technology path requires that the syngas components CO and $H_2$ be efficiently and economically dispersed or dissolved in the aqueous medium and transferred to anaerobic microorganisms that convert them to the desired products. And very large quantities of these gases are required. For example, the theoretical equations for CO or $H_2$ and $CO_2$ to ethanol are:

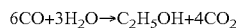

$$6CO + 3H_2O \rightarrow C_2H_5OH + 4CO_2$$

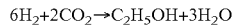

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol produced. Other products such as acetic acid and n-butanol have similar large stochiometric requirements for these gases.

Making biological production of alcohols or other liquid products from syngas commercially feasible requires the retention of large volumes of fermentation liquid. For example a singe commercial scale fermentation vessel may need to hold on the order of 4,000 cubic meters or more of fermentation liquid. These vessels will typically have a liquid depth of 15 to 20 meters or more. At such depths the hydrostatic pressure will exceed 150 to 200 kPa and would necessitate compression of the syngas stream to inject it as a feed to the lower portion of a deep fermentation vessel. Thus, there is a requisite need to compress (pressurize) the syngas and/or any tail or off-gas to be recycled from the top of the fermentation vessel to at least several atmospheres gauge. The use of large compressors complicates the operation of such system which in turn adds to the expense of such operations.

In addition to the need to pressurize the gas that enters the lower regions of deep tanks, the high pressure can also exacerbate the inhibitory effects of several of the syngas components. High dissolved concentrations of CO can inhibit the conversion of $H_2$ and as the CO concentration increases further it can inhibit the conversion of CO. Concentrations of dissolved CO tend to be difficult to maintain at the low levels needed especially during start-up when the biomass is in the growth phase, its initial concentration is low, and it has a low capacity to use the dissolved CO; the system is limited in gas uptake capacity of the bacteria and not mass transfer limited. As a result dissolved CO can build up more easily. The problem becomes more severe in deep tanks due to the resulting higher hydrostatic pressure which results in higher potential dissolved CO levels near the bottom of the fermentation vessel. In addition to the problem of high dissolved CO inhibiting conversion, high $CO_2$ concentrations can also have similar negative effects. Thus there is a need to control the concentrations of CO and $CO_2$ while still achieving good mass transfer needed to achieve the desired ethanol production rates.

Where the solubility of the gas components is limited as with CO and $H_2$, contacting and conversion of the gas stream components requires that the gas stream be well disbursed within the liquid medium as a fine dispersion to achieve the desired mass transfer rates between the gas phase and the conversion media (in this case the liquid phase). In the field of fermentation, the use of gas injection devices is known to disperse gas streams into liquids. Devices such as venturi injectors, slot injectors or jet injectors and other high pressure mixers may be used to create such gas-liquid dispersions. U.S. Pat. No. 4,683,122 shows the use of multiple jet nozzles positioned in the head space of a gas-liquid reactor for discharging a gas-liquid mixture into a lower portion of the reactor vessel. The primary input for reaction gas in the '122 reference requires compression of the gas supply. U.S. Pat. No. 4,426,450 discloses a fermentation vessel that uses a plurality of jet injectors to mix air and a fermentation broth in the bottom of a fermentation vessel. To maximize the duration of the gas bubbles in the liquid medium the dispersion gets released near the bottom of the fermentation vessel. Thus, the '450 reference requires a gas stream at sufficient pressure to overcome the hydraulic pressure of the liquid near the bottom of the vessel.

Highly dispersing the gas in the liquid aids in overcoming mass transfer limitations so that high rates of reaction are attainable. To this end the mixing of the liquid and gas desirably creates a high interface area between the two phases to maximize gas absorption as the gas components get transferred to and converted within the liquid phase. Reducing the size of the gas bubbles in the liquid, preferably to microbubbles, increases the interface area and aids in overcoming mass transfer limitations for the reaction or biological conversion. Once created, the microbubbles will begin coalescing into larger bubbles and gas slugs. Therefore, typical practice minimizes the transport of the gas dispersion from the point of its creation to its point of contact with the conversion media.

This dispersion of gas into a liquid stream is energy intensive and typically requires compression of the gas stream to at least the hydrostatic pressure of the fermentation vessel. Compressing a syngas stream poses special problems. Derivation of the syngas from biological sources may leave residual materials in the syngas that challenge the operation of compressors. For example the syngas may contain residual particulate material. Depending on the gasification operation that syngas may also contain high molecular weight hydrocarbons such as tars. Either of these materials can damage compressors that may be needed to create the necessary gas pressure to create high gas dispersion Likewise, compression of the tail or off-gas can have problems due to small particulates that can persist in the off-gas. In addition this gas stream will be saturated with water and there is the potential to have foam from the fermentation in the gas stream. All of these issues can make compression in a normal compressor difficult.

As a result commercial scale operations for the production of liquid products by fermentation from CO and $H_2/CO_2$ would benefit from process arrangements that can deliver feed gas streams such as syngas and/or recycled off gas from the fermentation vessel to the bottom of deep vessels for the joint purposes of achieving good gas transfer while controlling the dissolved concentrations of CO and/or $CO_2$ within desired limits. Preferably such process arrangements could do so without the need for large compressors. Therefore, processes are sought that can control the concentration of CO and $CO_2$ while reducing or eliminating the need for large compressors to deliver feed gas and/or recycled gas to the bottom of deep fermentation vessels.

SUMMARY OF THE INVENTION

This invention is a process for the biological conversion of a gas input stream comprising CO, $CO_2$ and $H_2$ into a liquid product in a deep fermentation vessel that reduces the dissolved concentration of CO and $CO_2$ in the vessel while also reducing compression requirements. The fermentation vessel of the process may retain fermentation liquid to depths of 20 meters or more. Off-gas from the fermentation vessel provides a diluent gas to reduce the concentration of CO in the gas stream entering the fermentation vessel. A recycle loop of recycle liquid containing the liquid product transfers the off-gas from the vessel into contact with the gas input stream. The recycle loop employs a gas injector (dispersion device), referred to as the "recycle injector," to recover the off-gas from the vessel and mix gas with the recycle liquid to create a gas-liquid dispersion. Pumping of the dispersion down to the lower elevation of the fermentation vessel raises the pressure of the dispersion without the need for external compressors.

The process simultaneously accomplishes control of both CO and $CO_2$ in the process gas streams. The gas input stream from an oxygen fed gasifier will typically contain 30% to 40% mole fraction of CO, up to 15% to 20% mole fraction of $CO_2$ and 30% to 40% mole fraction of $H_2$ with another 10% mole fraction of gases comprising $CH_4$, $N_2$, $NH_3$, $H_2S$ and other trace gases. The off-gas from the fermentation vessel will typically contain up to 10% mole fraction of CO, up to 75% mole fraction of $CO_2$, and up to 15% mole fraction of $H_2$ with the remainder of the off gas comprising up to 15% to 20% mole fraction of $CH_4$, $N_2$, $NH_3$, $H_2S$ and other trace gases.

For the instant invention, a liquid stream is pumped through a gas dispersion device located near the top of the deep fermentation vessel where the tail gas or off-gas is introduced into the liquid recycle stream at a much lower pressure compared to the hydrostatic pressure at the base of the vessel. The gas and liquid are mixed in the recycle injector into a fine gas/liquid dispersion. As the recycle loop pumps the off-gas and liquid mixture downward from the recycle injector the hydrostatic pressure increases and results in absorption of $CO_2$ into the liquid phase of the gas-liquid dispersion. A gas separation tank in a lower portion of the recycle loop receives the gas-liquid dispersion and the gas phase disengages from the liquid to provide a diluent stream that gets mixed with the feed gas stream and then injected into a lower portion of the fermentation vessel. A pump returns the recycle liquid from the gas separation tank to an upper portion of the recycle loop thereby lowering its hydrostatic pressure. The reduced pressure liquid flows into a $CO_2$ stripping vessel where release of a significant fraction of the dissolved $CO_2$ from the liquid is induced which produces a $CO_2$ rich tail gas stream for removal from the process. The recycle loop arrangement provides a highly efficient way of concurrently generating a gas stream with reduced $CO_2$ content from the off-gas stream that is also low in CO (since a high fraction of the CO is used in the fermentation vessel and the off-gas is low in CO as a result.) This now pressurized gas stream can be used for dilution of the CO concentration in the gas input stream and reduces the concentration of dissolved $CO_2$ that can be reached in the fermentation vessel since a significant amount of $CO_2$ compared to the overall mass generated is removed in the stripping vessel within the pumped flow loop.

The recycle loop provides a single stream that is used concurrently for absorption and compression. Compression of the gas-liquid dispersion may be increased by raising the elevation of the gas injection device, lowering the gas separation tank or a combination of the two.

The ability to absorb $CO_2$ is further enhanced by the degree of mixing in the gas liquid dispersion. This mixing is enhanced by the presence of the liquid product in the recycle stream. Liquid products such as alcohols, acetic acid, butyric acid and the like produced by the process have the added benefit of reducing the surface tension of the recycle liquid when present therein which results in generation of a much smaller bubble size compared to clean water. The recycle liquid can thus readily contain alcohol or other surface tension reducing chemicals that are introduced from the fermentation liquid or fractions thereof. As a result the recycle liquid with the surface tension modifying compounds allows generation of a gas-liquid dispersion at an elevated location and the presence of the liquid product will help keep the dispersion stable throughout its transport to lower elevation of the gas liquid separation tank. In this manner the off-gas gas stream passes at low pressure into contact with a circulating stream of the fermentation liquid and the gas components remain highly dispersed which improves absorption of $CO_2$ as the liquid travels down to gas separation tank.

In a broad form this invention is a process for converting a feed gas stream comprising CO, $CO_2$, and $H_2$ by contact with fermentation liquid into a liquid product. The liquid product reduces the surface tension of the fermentation liquid. The process retains an aqueous fermentation liquid comprising a liquid product and microorganisms in a fermentation vessel and introduces a feed gas stream into the fermentation vessel to convert the feed gas components to liquid products in the fermentation vessel by contact with microorganisms. Fermentation liquid is withdrawn from the fermentation vessel at a withdrawal point and pumped as a working fluid to a first gas injector. A gas input stream comprising a recycle gas stream passes to the first gas injector. A gas-liquid dispersion is discharged from the first gas injector into the fermentation liquid at a discharge point in a lower portion of the fermentation vessel. An off-gas comprising $CO_2$ is withdrawn from the fermentation vessel. A recycle liquid comprising water and the liquid product from a $CO_2$ stripper to a second gas injector. The process passes at least a portion of the off-gas into the second gas injector to produce an off-gas-liquid dispersion and transports the off-gas-liquid dispersion downwardly to compress the off-gas-liquid dispersion and absorb $CO_2$. The off-gas-liquid dispersion is collected in a gas separation tank from which the recycle gas is discharged. The recycle liquid is passed from said gas separation tank to the $CO_2$ stripper from which a $CO_2$ vent gas is removed.

In another form this invention is a process for converting a feed gas stream comprising CO, $CO_2$, and $H_2$ by contact with fermentation liquid into a liquid product wherein the liquid product reduces the surface tension of the fermentation liquid. The process retains an aqueous fermentation liquid comprising a liquid product and microorganisms in a fermentation vessel and withdraws fermentation liquid from the fermentation vessel at a withdrawal point and pumps the fermentation liquid as a working fluid to a first gas injector. A gas input stream comprising the feed gas stream and a recycle gas stream passes to the first gas injector. The gas injector discharges a feed gas-liquid dispersion into the fermentation liquid at a discharge point in a lower portion of the fermentation vessel and contact with microorganisms converts the feed gas components to liquid products in the fermentation vessel. The process withdraws off-gas comprising $CO_2$ from the fermentation vessel, passes a recycle liquid comprising water and the liquid product from a $CO_2$ stripper to a second gas injector, and passes off-gas into the second gas injector to produce an off-gas-liquid dispersion. Downward transport of the off-gas-liquid dispersion compresses the off-gas-liquid dispersion and absorbs $CO_2$. A gas separation tank collects the off-gas-liquid dispersion and discharges a recycle gas therefrom. At least a portion of the feed gas passes into at least one of the recycle gas or the off-gas to provide the gas input stream to the fermentation vessel. The recycle liquid passes from the gas separation tank to the $CO_2$ stripper that removes $CO_2$ therefrom and discharges the stripped $CO_2$ as a ventgas stream or $CO_2$ tail gas stream.

In another form the invention can reduce compression requirements for the feed gas stream as well as the off-gas stream. For example the recycle injector in the recycle loop can receive both the off-gas stream and the feed gas stream. The recycle injector then discharges the gas mixture as a fine gas liquid dispersion. Mixture of the off-gas stream dilutes the feed gas stream to reduce the concentration of CO. At the same time mixture of the streams effects absorption of $CO_2$ from both the off-gas and feed gas streams.

When the gas-liquid dispersion reaches the gas separation tank, the tank discharges a recycle stream that contains the feed stream and serves as the gas input stream. The tank can be located low enough relative to the fermentation vessel to give the retained feed gas stream sufficient pressure to enter a gas injector, referred to as the "vessel gas injector," that discharges a dispersion of fermentation liquid and feed gas into a lower portion of the fermentation vessel. The gas input stream and the recycle gas stream can be mixed together in a common recycle injector or directed to different recycle injectors that feed into the same gas transporting conduit and/or same gas separation tank and employ the same subsequent $CO_2$ stripping tank.

The recycle loop of this invention can be used to obtain the commercial advantages of reducing any needed compression of the gas streams to the point where an ordinary blower can supply any needed pressure for dispersion of the gas into the recycle liquid. By injecting a gas stream at lower pressure into a mixing device and using the liquid stream as the primary energy input to the recycleinjector, this invention can achieve the intensity of mixing and supply the shear forces necessary to cause good mixing and dispersion of the gas stream within the liquid to create a dispersion stream of small bubbles within the liquid. Thus, this invention can also accomplish the elimination of compressors by adjusting the elevations of the gas mixing device that creates the dispersion stream with respect to the disengagement point of the gas from the liquid.

Therefore, in one aspect of the invention the fermentation liquid can contain a liquid product with properties for stabilizing the dispersion of the gas in the liquid. In particular the presence of alcohol in the fermentation liquid in conjunction with the use of the recycle injector allows the transport of the dispersion stream over a significant vertical distance without coalescing of the gas bubbles. Thus, the invention places the recycle injector that creates the dispersion of gas and liquid at a relatively high elevation with respect to the elevation of the gas separation tank where the gas-liquid dispersion gets separated into gas and liquid. Keeping the recyle injector relatively higher than the separation point for the dispersion stream allows a lowering of the inlet pressure for the gas entering the recycle injector. The pressure of the mixed phase stream containing the gas increases hydraulically as it flows downward.

The hydraulic head of liquid created by the injection of the gas-liquid dispersion into the gas separation tank at a lower elevation than the recycle injector eliminates the need for additional pressure on the outlet side of the recycle injector. The downward transport of the gas liquid dispersion in a confined conduit creates a static pressure head that compresses the gas liquid dispersion before it enters the vessel. Injection of the off-gas and optionally the gas input into the fermentation liquid does lower the density of the gas-liquid dispersion in the conduit relative to the fermentation vessel liquid. Raising the outlet pressure of the recycle injector can compensate for any loss in static pressure at the discharge point where the gas-liquid dispersion enters the fermentation vessel. The pressure of the gas-liquid dispersion at the gas separation tank may also be raised by elevating the recycle injector location relative to the gas separation tank. Elevating the recycle injector adds static pressure to the gas-liquid dispersion over its increased height thereby increasing the pressure of the dispersion stream at the discharge point.

This raising of the recycle injector elevation does not increase the liquid side pressure required in the recycle injector. As a result the gas phase still enters the recycle injector at a relatively low pressure. The invention can thereby eliminate or reduce the need for compression of the gas stream to the point where a compressor is not required. Instead, the pumping of the fermentation liquid as the motive fluid for mixing of the gas stream and the downward transport of the dispersion stream provides all of the necessary pressure to mix the off-gas stream with the feed gas stream or to supply the gas input stream to the vessel gas injector of the fermentation vessel. In this manner the process effectively uses the height difference between the recycle injector location and the gas separation tank to raise the pressure of the gas-liquid dispersion and eliminate the need for a compressor to supply feed gas to the process.

The invention may be used in any arrangement of a bioreactor that receives a feed gas comprising CO and produces an off-gas comprising $CO_2$, $H_2$ and other trace gases. The invention is most useful for bioreactors that retain a significant volume of a liquid medium over an extended vertical distance. This Invention finds particular application to arrangements that suspend microorganisms in vertically extended vessels such as bubble column arrangements or stirred tank reactors. Another form of bioreactor uses a suspended media in a liquid volume and is shown in US Patent Application publication no. 20090035848

This invention is particularly useful for the conversion of gas streams comprising components of syngas in a fermentation liquid. Ordinarily the fermentation liquid will comprise water, microorganisms suspended therein, nutrient chemicals, cell debris from the microorganisms and products produced by the metabolic processes of the microorganisms. The low solubility of the CO and $H_2$ in the primarily aqueous fermentation liquid necessitates a very good dispersion of the gas into the liquid to achieve good mass transfer so that high conversion is efficiently obtained. The inherent presence of various organic compounds from such biological conversions, mostly ethanol, has been found to provide a highly beneficial combination in achieving good gas dispersion with the process arrangement of this invention.

DETAILED DESCRIPTION OF THE INVENTION

Figure 1:
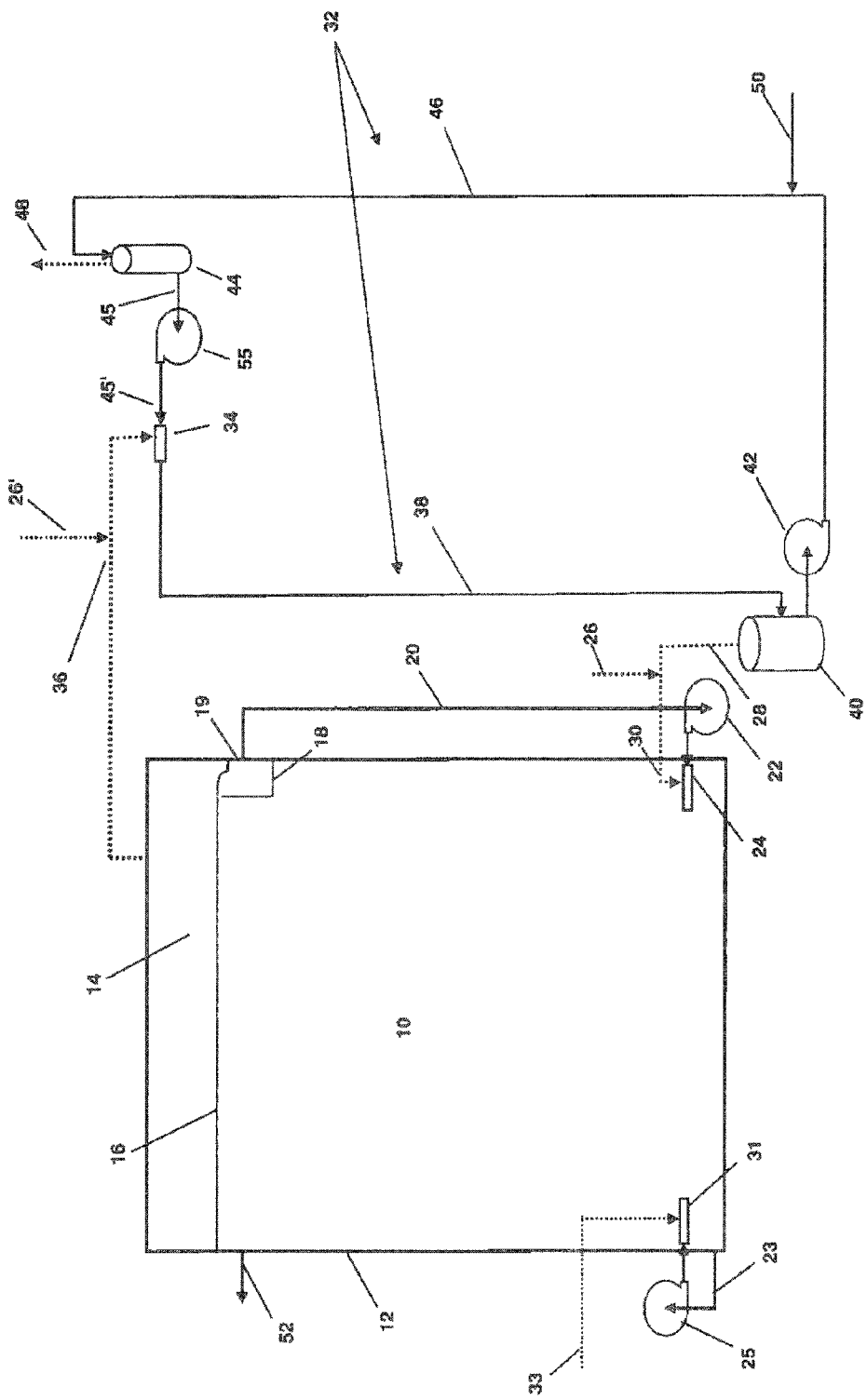
FIG. 1 is a schematic drawing showing a fermentation column and the recycle loop of this invention.

This invention may be used in fermentation processes for the production of liquid products from a gas stream containing CO, $CO_2$ and $H_2$ where the fermentation zone produces an off-gas stream comprising a higher mole fraction of $CO_2$ and a lower mole fraction of CO and $H_2$ and liquid products that reduce the surface tension of the fermentation liquid. The invention is particularly applicable to those processes that produce low molecular weight alcohols and corresponding acids such as ethanol, propanol, n-butanol, acetic acid, propionic acid and butyric acid as liquid products in the fermentation liquid. Especially useful processes for application of the invention are those that produce ethanol or acetate in a concentration of at least 0.05 wt %.

Many sources of CO, and $CO_2$ and $H_2$ exist. For example, sources of such gases are "waste" gases such oil refinery waste gases, gases (containing some $H_2$) which are produced by yeast fermentation, gasified cellulosic materials, coal gasification, reformed natural gas etc. Alternatively such gases are not necessarily produced as by products of other processes but may be produced specifically for use in the fermentation reactions within the fermentation vessel. Preferably the preferred source of the CO, $CO_2$ and $H_2$ is syngas and more preferably syngas produced by gasification of readily available low-cost agricultural raw materials, or waste materials such as municipal solid waste, expressly for the purpose of the bacterial fermentation.

The fermentation liquid will comprise an aqueous suspension of acetogenic microorganisms and various media supplements retained in a fermentation vessel. Suitable microorganisms generally live and grow under anaerobic conditions, meaning that dissolved oxygen is essentially absent from the fermentation liquid. The various media supplements may comprise buffering agents, low levels of certain trace metals, vitamins, salts etc. Adjustments in the media may induce different conditions at different times such as growth and non-growth conditions which will affect the productivity of the microorganisms. US 2008/0057554 A1, the contents of which are hereby incorporated by reference further discloses the conditions and contents of suitable fermentation liquid for bioconversion CO and $H_2/CO_2$ using anaerobic microorganisms.

Bioconversions of CO and $H_2/CO_2$ to acetic acid, n-butanol, butyric acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid and *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351. All of these references are incorporated herein in their entirety.

These microorganisms all have the capacity to produce liquid products that will reduce the surface tension of the fermentation liquid in the fermentation vessel. In application of this invention to the conversion CO or a mixture of $CO_2$ and $H_2$ the fermentation vessel will typically comprise a bioreactor that retains the microorganisms suspended in the fermentation liquid either as planktonic cells, cell aggregates or floc particles or attached or otherwise contained on or in a carrier particle that is retained within the fermentation vessel. Specific types of bioreactors include bubble column bioreactors and stirred tank bioreactors.

The method is enhanced by the presence of the product liquid in the fermentation broth that serves as a surface acting agent that lowers the surface tension to overcome the tendency of the bubbles to coalesce thereby avoiding bubble agglomeration into larger bubbles (coalescence) which reduces the interfacial surface area of the dispersed gas as it travels to a lower elevation of the discharge point. In particular it has been observed that the presence of oxygenates such as ethanol and/or organic acid in the liquid media at concentrations as low as 0.05 wt % have a profound effect on gas transfer efficiency. In clean water the result of the adding the surface tension agent can provide gas transfer rates of up to 3 times that observed for clean water. The combination of the alcohol as the surface acting agent together with the intense mixing at the elevated recycle injector location gives the surprising result of sustaining good dispersion of the gas in the liquid as it travels over distances in excess of 20 meters to the gas separation tank. For example alcohols are known to serve as an effective surface acting agent in dispersion of gas into microbubbles within aqueous solutions. In particular the lower surface tension and smaller bubble size resulting from the presence of the alcohol in the resulting fermentation broth can, in concert with maintaining a sufficient downward velocity in the confining conduit through which it flows, largely overcome any problems of rapid bubble coalescence downstream of the recycle injector. Preferably the alcohol is at a total concentration of at least 0.05 wt %. The ability of the liquid product to reduce the surface tension avoids the need to add other suitable agents to control surface tension and thereby avoids any deleterious interactions with other substances in the column of liquid that could potentially inhibit desired conversions within the fermentation vessel or contaminate products that are generated. Thus this invention works well with processes for the fermentation of gas phase feed especially CO or a mixture of $CO_2$ and $H_2$ and where microorganisms in the column of liquid convert these gas components to alcohol, in particular ethanol.

The invention is best suited for use in combination with a fermentation vessel that provides a substantial depth of fermentation liquid. The fermentation vessel will typically rise to a height of at least 10 meters, more typically to height of 15 meters and most often to a height of 20 meters or more. The depth of the fermentation liquid will occupy either the full height or nearly the full height of the fermentation vessel. This vessel height will establish a hydrostatic pressure gradient along the vertical profile of the vessel. The retained gas stream captured from the dispersion of gas and liquid in the dispersion stream must overcome this hydrostatic pressure at the point where it enters the vessel via the gas injection device. Thus where the gas-liquid dispersion enters at a discharge point located 10 meters or more below the liquid surface, the static pressure head inside the vessel would equal approximately 100 kPa gauge and for a liquid height of 15 meters the static pressure head would equal approximately 150 kPa gauge.

Use of the invention requires a process arrangement that provides a downward flow of the liquid and entrained gas from the outlet of the recycle injector located in the recycle loop. The liquid in the recycle loop comprises water and one or more products from the fermentation zone. Liquid for the recycle loop typically comprises the fermentation liquid or a fraction of the fermentation liquid obtained from a product recovery zone. The gas-liquid dispersion flows from the recycle injector in a dispersion conduit that confines the gas and liquid. The dispersion conduit supplies a static pressure head equal to the weight of the gas-liquid dispersion over the difference in elevation between the recycle injector outlet and the gas separation tank. For most recycle loops the difference in elevation between the recycle injector and the gas separation tank will equal at least 10 meters. The dispersion conduit will typically have a uniform flow area over its length to keep the gas-liquid dispersion from expanding in volume.

A general understanding of the invention and its application is most readily seen in FIG. 1 that shows a vertically extended column of fermentation liquid 10 in a vessel 12. Vessel 12 traps a volume 14 of off-gas above a liquid surface 16. FIG. 1 schematically shows a process arrangement for the invention that omits equipment that is not essential for an understanding of the invention. A collector 18 provides a location for supply of fermentation liquid to a withdrawal point 19 for removing liquid 10 from the fermentation vessel 12. The withdrawal point 19 is shown proximate the liquid surface in FIG. 1 but can practically be located anywhere along the vertical profile of the fermentation vessel. The collector can provide a means for initially filtering cell material from the fermentation liquid to reduce the amount of microorganisms and organic debris in the liquid withdrawn from the vessel. A conduit 20 carries the liquid from withdrawal point 19 to a pump 22. Pump 22 delivers the fermentation liquid to a vessel gas injector 24. Pressurized gas from line 28 mixes with a feed gas stream 26 to form a gas input stream that flows to the vessel gas injector 24 via line 30. Vessel gas injector 24 discharges a gasliquid dispersion into the fermentation liquid 10.

Alternatively, the feed gas stream may enter the fermentation vessel independently of the gas input stream. FIG. 1 shows such an alternate arrangement wherein a line 23 removes fermentation liquid as a working fluid for entry into a pump 25 that discharges the fluid into a feed gas injector 31. In this alternate arrangement a line 33 supplies feed to feed gas injector 31 that discharges a dispersion of feed gas and fermentation liquid into liquid 10.

Off gas from volume 14 enters a recycle loop 32 via a recycle gas injector 34. A line 36 delivers off-gas from vessel 12. Circulating recycle liquid supplies the motive force to recycle injector 34 for dispersing the off-gas into the recycle liquid. Recycle liquid flows downward in a dispersion conduit 38 to deliver the gas dispersion in the recycle liquid to a gas separation tank 40.

The dispersion conduit 38 will charge the gas-liquid dispersion into the gas separation tank. The gas separation tank 40 will have a level control that maintains a suitable gas-liquid interface to effect degassing of the gas-liquid dispersion. Additional degassing structures may reside in the gas separation tank such as baffles and distributors to aid in the separation of the gas from the liquid.

Recycle injector 34 is located above the level 16 of liquid in vessel 12 and the gas separation tank 40 has an elevation below vessel 12. Gas entrainment in the gas-liquid dispersion stream lowers its density and reduces the static pressure head of the fluid in the dispersion conduit. A higher elevation of the recycle injector relative to the upper surface of the liquid in the vessel raises the static pressure head of the lower density fluid that makes up the gas liquid dispersion. The difference in elevation from the gas separation tank to the recycle injector can provide enough static head of liquid to pressurize the recycle gas in line 28 as needed for flow to the vessel gas injector 24.

Recycle liquid from tank 40 flows to a pump 42 that pumps the recycle liquid through a line 46 and up to a $CO_2$ stripper 44. Reduced pressure of the recycle liquid in the $CO_2$ stripper causes a release of the dissolved $CO_2$, that is now above saturation at this lower pressure, from the recycle liquid. This released $CO_2$ flows out of line 48 as a $CO_2$ tail gas or vent gas stream. Lines 45 and 45' carry the $CO_2$ deficient liquid from the stripper 44 to through a pump 55. Pump 55 that provides the necessary pressure to the recycle injector 34.

A conduit 52 withdraws liquid from the vessel 10 for delivery to a product recovery zone (not shown). The product recovery zone will consist of known equipment arrangements for removal of residual cell material, separation and recovery of liquid products from the fermentation liquid, return of recovered fermentation liquid and purging of waste streams and materials. Suitable equipment arrangement can include filters, distillation columns, membrane systems and other separation equipment. US 2009/0215139 A1 shows an arrangement for a product recovery zone that recovers an ethanol product from a bioreactor. Those skilled in the art can provide suitable equipment to separate the fermentation liquid into a liquid product stream for recovery as product and to generate any needed purge stream and recycle streams.

Recycle loop 32 will lose small amounts of liquid with gas streams that flow through lines 28 and 48. Line 50 supplies make-up liquid to the recycle loop. The make-up liquid can comprise fermentation liquid from vessel 10. Suitable streams that contain liquid product may also be obtained from a variety of locations in the product recovery section.

Figure 2:
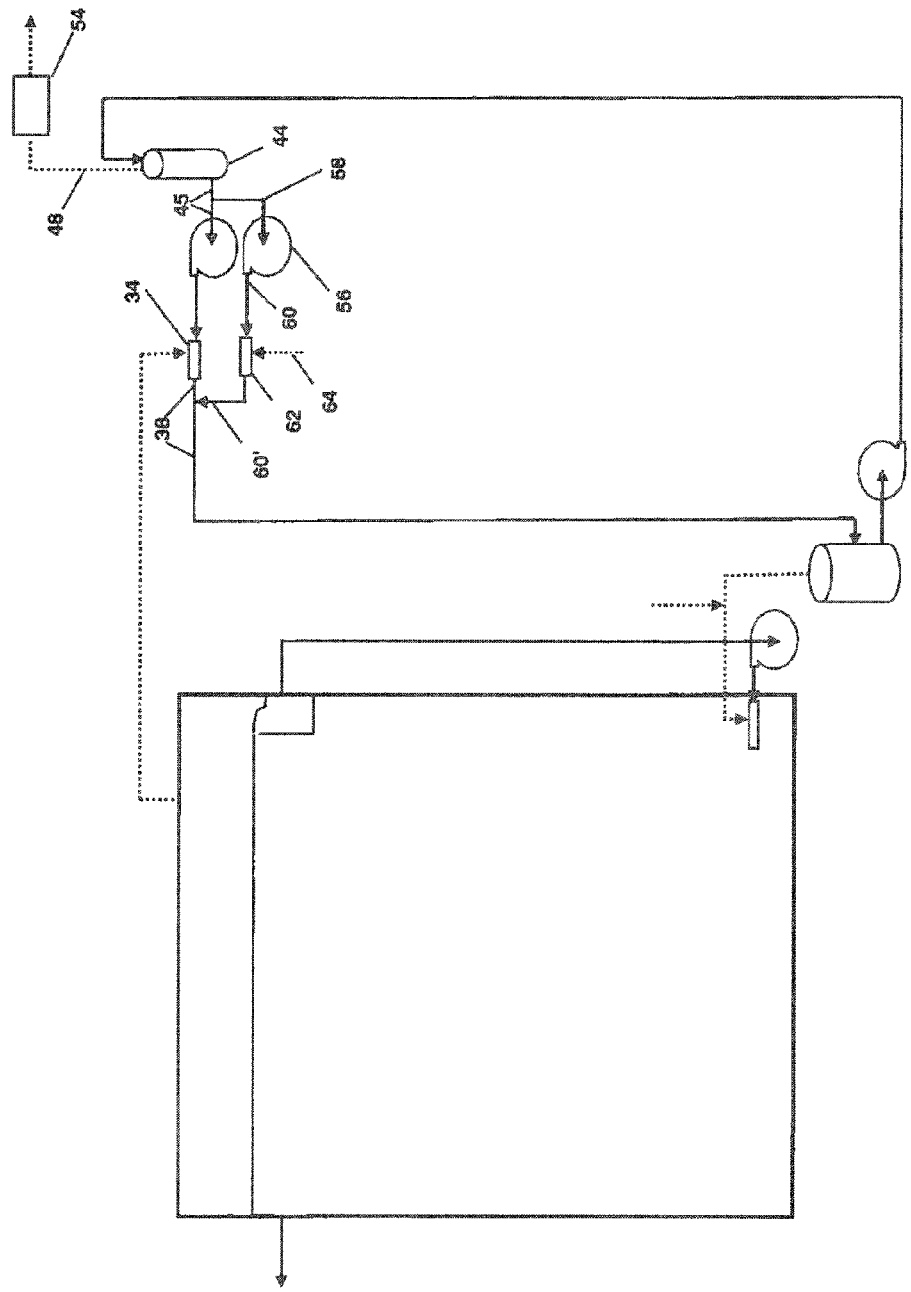
FIG. 2 is a schematic drawing showing a variation to the fermentation column and the recycle loop of FIG. 1.

The recycle loop of this invention can effect a substantial reduction in the CO and $CO_2$ concentration in the gas fed to the fermentation vessel. The reduction of the CO concentration will depend on the amount of off-gas, lean in CO, that is recycled to dilute the input or feed gas. Absorption and removal of the $CO_2$ in the recycle loop changes the relative composition of the gas. The off-gas before using this system may include from 60 to 75% mole fraction of $CO_2$. The recycle loop may remove on the order of 30 to 70 percent of the $CO_2$ which reduces the mole fraction of the tail gas to 15 to 35% mole fraction. The CO content of the scrubbed, recycled gas will generally be between 15 and 25% mole fraction so will provide some dilution of the incoming feed gas depending on the relative volume of off-gas recycled Further removal of $CO_2$ may be effected by the arrangement shown in FIGS. 2. In FIG. 2 the use of equipment for the enhancement of the gas release by putting the $CO_2$ stripper under partial vacuum is shown. In this arrangement a vacuum pump 54 withdraws effervesced or released gas from the $CO_2$ stripper 44 through conduit 48. The use of the vacuum pump arrangement can remove up to 90% of the $CO_2$ from the off-gas and effect a further reduction in the concentration of $CO_2$ in the fermentation vessel.

Additional removal of $CO_2$ may also result from the use of the alternate feed point for the gas input stream shown in FIG. 1. Instead of supplying the feed gas to the recycle gas via line 26 or optionally line 33 as previously described, all or a portion of the input gas can flow through line 26' in admixture with the off-gas in line 36. Charging the feed to this point provides the immediate advantage of causing absorption of $CO_2$ from the feed gas stream as well as the off-gas stream. Thus, the gas separation tank 40 now discharges a gas input stream at sufficient pressure to supply it to vessel gas injector 24.

An added advantage of supplying the gas input through line 26' is a lower pressure requirement for the feed gas stream. The higher elevation of recycle injector 34 reduces the required input pressure for the gas streams that enter therein. Accordingly, feed gas stream 26' can flow to the recycle injector without the need for significant compression by again using the recycle liquid as the primary motive liquid to create a good gas-liquid dispersion from the recycle injector 34.

The recycle injector creates the gas-liquid dispersion and promotes good mixing of the gas and liquid to disperse the gas as bubbles into the liquid phase. Typical gas injectors include a venturi eductor, a jet injector, or a slot injector. These devices use the liquid flowing through them as the motive liquid and, in accordance with this invention, as the primary means of delivering the energy necessary to create high shear and good dispersion of gas bubbles in the exiting stream. Suitable devices for this invention will use the liquid stream as the primary motive force through the injection device.

Providing the required pressure drop for suitable mixing will comprise one of the main energy inputs into the operation of this process. Pressure drop across these devices will generally range from 100 to 400 kPa. This pressure drop will provide the main energy input for dispersing the gas into microbubbles and in some cases will also serve to induce gas flow into the injection device.

Preferred gas injectors will operate with low requirements for input gas pressure. In most cases the input gas pressure will not exceed 100 kPa and input pressures of 40 kPa or less may be used. Arrangements of the invention as shown herein and as readily appreciated by those skilled in the art can operate with gas pressure at atmospheric or only slightly higher than atmospheric pressure. Operating with some positive gas stream pressure into a gas injector can provide a significant increase in the amount of gas that can be fed to the gas injection device and can improve the mixing that is achieved therein while still operating the gas injector well below the pressure that would require a compressor to deliver gas to the gas injector.

The property of the liquid product in reducing the surface tension of the fermentation liquid significantly increases the volume of gas that can be entrained with the liquid in the gas injector. This enables the gas injector to receive higher volumes of input gas or recycle gas from the vessel. Typically the ratio of gas to the liquid entering the gas injector is from 1/1 to 3/1 actual $m^3/m/m^3/m$.

Another important operating parameter of a gas injector is the exit velocity of the gas-liquid dispersion. This invention uses a difference in elevation between the outlet of the recycle injector and gas separation tank to reduce the required discharge pressure on the outlet of the device. Higher exit velocities on the outlet of the recycle injector minimize the time for bubble coalescence before the gas-liquid dispersion gets to the gas separation tank. Velocity of the gas-liquid dispersion downstream of the recycleinjector is usually in the range of 0.05-2 meters/second. Preferably the gas-liquid dispersion will have an average velocity of at least 1 meter/second between the recycleinjector outlet and the gas separation tank.

Venturi eductors generally have the advantage of providing the most pressure drop for purposes of drawing gas streams into the gas injector. Venturi devices will allow use of low pressure gas streams or, depending on the elevation of the venturi device, the gas stream may enter the recycleinjector at atmospheric pressure.

Jet aerators or slot injectors are another suitable form of gas injection device. Slot injectors are a variant of jet aerators. These devices can operate as venturi devices that draw gas into the device for mixing without supplying a positive gas pressure. These devices may also operate with some positive pressure of the gas stream such that gas at relatively low pressure enters a mixing chamber with a high velocity liquid stream for contact and intense mixing of the liquid under high shear conditions. This results in the formation of micron sized bubbles or microbubbles for injection into the vessel as the dispersion stream. The microbubbles are relatively fine (0.1 to 1.0 mm in diameter) and their presence aids in dissolving some of the gas into solution with the liquid medium.

In FIG. 2 an additional pump 56 can in one arrangement provide additional water flow to mix with the recycled gas. This flow can be added directly downstream of the recycle injector 34, via lines 60 and 60', and used to create the gas/liquid dispersion to minimize the amount of pumping energy required.

Alternatively pump 56 may be used to provide energy for a separate gas injector and gas input stream. FIG. 2 also shows an optional gas injector 62 between lines 60 and 60'. This injector 62 can provide an additional point of entry and mixing for the feed gas or any other gas stream via line 64. Use of the additional injector 62 allows recycle gas to enter via line 36 at a different pressure than the gas that enters injector 62.

Figure 3:
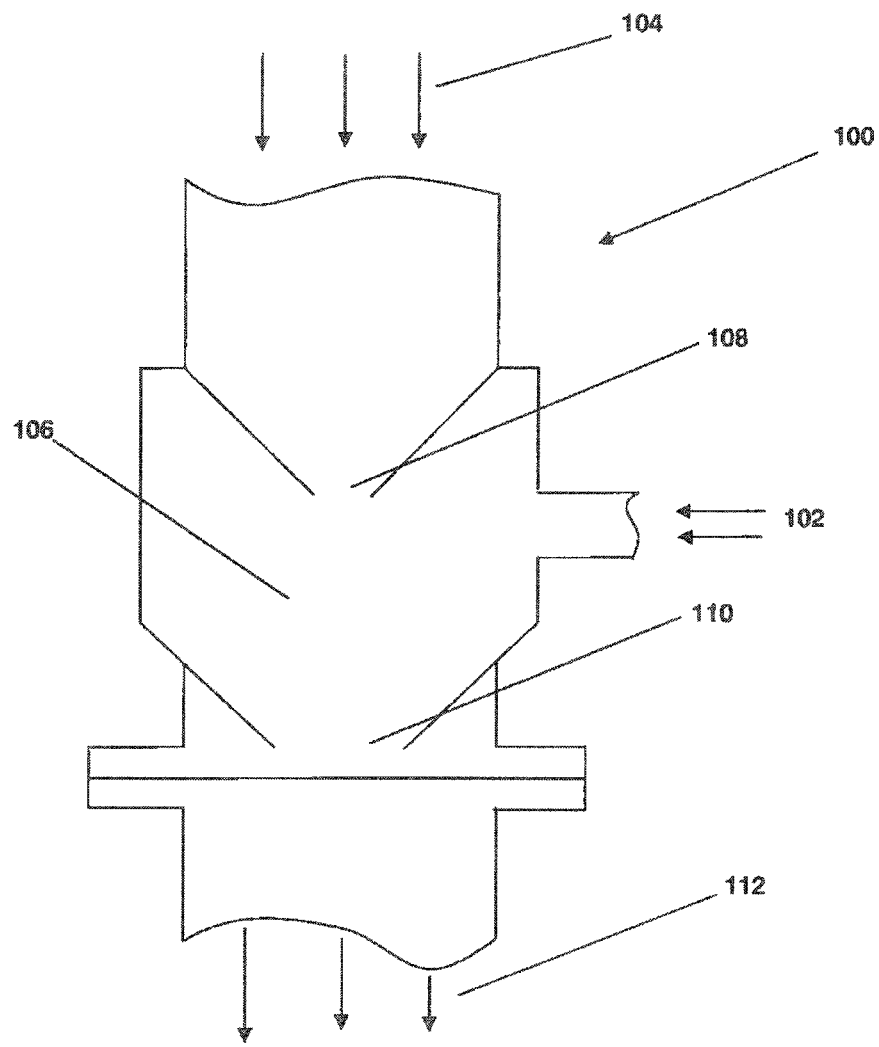
FIG. 3 is a schematic drawing of an internal arrangement for a gas injection device.

FIG. 3 shows the typical internal arrangement of a gas injector 100 in more detail. The injector has an inlet for gas stream 102, an inlet for liquid stream 104, and a mixing zone 106, into which the liquid stream 104 is discharged through an orifice 108. The gas stream 102 meets the liquid stream 104 in the mixing chamber 106 from which a dispersion 112 exits via an outlet orifice 110. Many types of gas injectors are known and commonly used industrially. One model of a preferred type of gas injector is shown in U.S. Pat. No. 4,162,970.

The required difference in elevation from the outlet of the recycle injector on the recycle loop to the gas separation tank will vary depending on the type of gas injection device, the quantity of gas for injection, the properties of the liquid and other factors particular to the type of contacting required by the recycle liquid. The invention usually provides greater benefits as the elevation difference from injector outlet to the gas separation tank increases. Typically the difference in elevations equals at least 10 meters and more preferably at least 15 meters. In a preferred arrangement the recycle injector will have a location above the highest liquid level in the fermentation vessel.

The process of this invention may supply all of the gas requirements for contact in the liquid column or additional gas may be added by other gas injection means such as bubble aeration systems. Where the gas-liquid dispersion enters the liquid column or vessel it will usually do so as a high velocity plume that keeps the bubbles in the highest hydrostatic pressure for a longer time and results in greater gas transfer. The dissipation of the energy in the plume as it expands creates fine eddy currents that help mix any other materials contained in the column of liquid.

EXAMPLE 1

A 36, $m^3$ fermentor in the form of a fermentation vessel having a 1.05 meter diameter and a 16 meter liquid depth is used as a fermentation vessel for the conversion of carbon monoxide and hydrogen and carbon dioxide into ethanol. The fermentation medium having the composition given in Table 1 is used to fill the fermentor and maintained at about 37° C. The fermentor is maintained under anaerobic conditions.

The bioreactor system is operated with an active culture of *Clostridium ragsdalei* ATCC No. BAA-622. The fermentation pH is maintained at a pH in the range of 5.0 to 5.3 to favor ethanol production.

TABLE 1

Fermentation Medium Compositions

| Components | Amount per liter |
| --- | --- |
| Mineral solution | 25 ml |
| Trace metal solution | 10 ml |
| Vitamins solution | 10 ml |
| Yeast Extract | 0.05 g |
| Adjust pH with NaOH | 6.1 |
| Reducing agent | 2.05 ml |

A gas input stream having a composition of about 38.6% mole fraction CO, 38.05 mole fraction % $H_2$, 18.2% mole fraction $CO_2$ and 4.7% mole fraction trace and inert gases ($N_2$, $CH_4$ etc.) is fed to the fermentation vessel pressurized via a bottom mounted gas injector. With no gas scrubbing the off gas has a composition of 8.8% mole fraction CO, 12.2% mole fraction $H_2$, 68.4% mole fraction $CO_2$ and 10.6% mole fraction trace gases. The headspace in the fermentation vessel is maintained under a slight pressure of approximately 15 kPa.

The off-gas is collected and recycled through a slot injector located at an elevation of approximately 18 meters. The system is operated with a combined flow of 1175 liters per minute (415 liters per minute through the nozzle as the motive force and 660 liters per minute of flow added after [directly downstream of] the slot injector to increase flow in contact with the gas/liquid dispersion) for scrubbing $CO_2$ according to the instant invention. The additional 660 liters per minute adds significant extra adsorptive capacity at a low energy cost.

Pressure drop across the injector is approximately 130 kPa gauge. The slot injector produces a gas-liquid dispersion that flows 18 meters downward through a 10 cm diameter confining conduit and into a gas separation tank. The gas-liquid dispersion separates in the gas separation tank into a recycle gas stream described below and the recycle liquid. The liquid is 95% saturated with $CO_2$ at the static pressure and mole fraction of $CO_2$ at the gas separation tank. A pump transports the recycle liquid back to the top of the recycle loop and into a $CO_2$ stripper. In the $CO_2$ stripper the dissolved $CO_2$ is removed to approximately 115% of saturation at that pressure (approximately atmospheric) removing approximately 800 kg/d of $CO_2$, which is equivalent to 84% of the combined mass of $CO_2$ entering with the syngas and that produced via the anaerobic fermentation. Recycle liquid from the $CO_2$ stripper is re-pumped back to the slot injector and used to create the gas/liquid dispersion to complete the recycle loop.

Once the system equilibrates the off-gas has a composition of 20.6% mole fraction CO, 28.7% mole fraction $H_2$, 26.0% mole fraction $CO_2$ and 24.7% mole fraction trace and inert gases.

What is claimed is:

1. A process for converting a feed gas stream comprising feed gas components of CO, $CO_2$, and $H_2$ into a liquid product by contact with an aqueous fermentation liquid wherein the liquid product reduces the surface tension of the fermentation liquid, said process comprising:
   a) retaining a portion of the aqueous fermentation liquid in a fermentation vessel;
   b) producing said liquid product by contact of the feed gas stream with microorganisms suspended in the aqueous fermentation liquid and retained in the fermentation vessel;
   c) withdrawing aqueous fermentation liquid containing the liquid product from said fermentation vessel at a withdrawal point on said fermentation vessel to provide a withdrawn aqueous liquid;
   d) recovering the liquid product from the withdrawn aqueous fermentation liquid of step c) in a separation zone to recover the liquid product and to recover aqueous fermentation liquid;
   e) returning a first portion of the recovered aqueous fermentation liquid from step d) to the fermentation vessel and passing a second portion of the recovered aqueous fermentation liquid from step d) to a recycle loop that continuously circulates a recycle liquid therein;
   f) recovering an off-gas stream from a gas phase located at an upper portion of the fermentation vessel;
   g) passing the off-gas stream and the recycle liquid of step e) to a first gas-liquid injector located at a first elevation and discharging a first gas and liquid mixture from the first gas-liquid injector into the recycle liquid of step (e);
   h) pumping the recycle liquid from the first gas liquid injector downward for a distance of at least 10 meters to a gas separation tank located at a second elevation, recovering a diluent gas from the gas separation tank and passing the recycle liquid from the gas separation tank back into the recycle loop;

i) pumping the recycle liquid from the gas separation tank upward in the recycle loop to a stripping vessel, recovering a $CO_2$ containing gas from the stripping vessel and passing the recycle liquid from the stripping vessel back into the recycle loop and to the first injector of step g), j) pumping at least one of the first portion of aqueous fermentation liquid from step (e) and a stream of aqueous fermentation liquid withdrawn from the fermentation vessel together with the diluent gas of step h) to a second gas-liquid injector and discharging a second gas and liquid mixture into a lower portion of the fermentation vessel at discharge point located on the fermentation vessel at a third elevation that is below the first elevation of step g) and above the second elevation of step h); and, k) adding at least a portion of the feed gas stream by at least one of: direct addition to the fermentation vessel; addition to the off-gas stream of step f); and, addition to the diluent gas for injection into the fermentation vessel with the diluent gas as described in step h).

2. The process of claim 1 wherein the downward transport of the recycle liquid generates a static pressure head at least equal to the static pressure head generated at the discharge point by the fermentation liquid in the fermentation vessel.

3. The process of claim 1 wherein the liquid product comprises at least one of ethanol, propanol, n-butanol, acetic acid and butyric acid.

4. The process of claim 1 wherein the aqueous fermentation liquid comprises ethanol and/or acetate at a total concentration of at least 0.05 wt %.

5. The process of claim 1 wherein the liquid product comprises alcohol and the aqueous fermentation liquid contains alcohol at a total concentration of at least 0.05 wt %.

6. The process of claim 1 wherein the $CO_2$ containing gas of step i) is withdrawn under vacuum conditions from the $CO_2$ stripping vessel.

7. The process of claim 1 wherein the second gas injector comprises one of a venturi-type eductor, a jet injector, and a slot injector.

8. The process of claim 1 wherein the microorganisms comprise a mono-culture or a co-culture of any of *Clostridium ragsdalei, Butyribacterium methylotrophicum, Clostridium Ljungdahli, Clostridia Coskatii* and *Clostridium Autoethanogenum*.

9. The process of claim 1 wherein at least a portion of the feed gas stream enters the vessel by direct injection into the fermentation vessel with aqueous fermentation liquid withdrawn from the fermentation vessel through a third gas-liquid injector that discharges a mixture of aqueous fermentation liquid and feed gas into the fermentation vessel.

10. The process of claim 1 wherein at least one of a portion of the feed gas stream or a portion of the liquid product is added to the recycle liquid in the recycle loop.

\* \* \* \* \*